(12) United States Patent
Yi et al.

(10) Patent No.: US 11,116,600 B2
(45) Date of Patent: Sep. 14, 2021

(54) MEDICAL ARM ASSEMBLY

(71) Applicants: KOH YOUNG TECHNOLOGY INC., Seoul (KR); INDUSTRY-UNIVERSITY COOPERATION FOUNDATION HANYANG UNIVERSITY ERICA CAMPUS, Ansan-si (KR)

(72) Inventors: Byung Ju Yi, Bucheon-si (KR); Jae Hong Woo, Ansan-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 12 days.

(21) Appl. No.: 16/313,276

(22) PCT Filed: Aug. 31, 2018

(86) PCT No.: PCT/KR2018/010174
§ 371 (c)(1),
(2) Date: Dec. 26, 2018

(87) PCT Pub. No.: WO2019/045530
PCT Pub. Date: Mar. 7, 2019

(65) Prior Publication Data
US 2021/0220082 A1 Jul. 22, 2021

(30) Foreign Application Priority Data
Sep. 1, 2017 (KR) .................. 10-2017-0111864

(51) Int. Cl.
*A61B 90/50* (2016.01)
*A61B 34/30* (2016.01)

(52) U.S. Cl.
CPC .............. *A61B 90/50* (2016.02); *A61B 34/30* (2016.02)

(58) Field of Classification Search
CPC combination set(s) only.
See application file for complete search history.

(56) References Cited

U.S. PATENT DOCUMENTS 5,800,423 A 9/1998 Jensen
5,817,084 A 10/1998 Jensen
(Continued)

FOREIGN PATENT DOCUMENTS

CN 101548904 10/2009
CN 102218734 10/2011
(Continued)

OTHER PUBLICATIONS

Chinese Office Action, with English translation, corresponding to Chinese Application No. or Publication No. 201880002557.5, dated Feb. 26, 2021.
(Continued)

*Primary Examiner* — Scott Luan
(74) *Attorney, Agent, or Firm* — Kile Park Reed & Houtteman PLLC

(57) ABSTRACT

A medical arm assembly according to an embodiment disclosed includes: a remote joint where a remote point is located; a positioning arm section configured to support the remote joint, move the remote joint that a position of the remote point relative to the reference point is changed only in the direction of a virtual reference straight-line through the reference point and the remote point, and fix the relative position of the remote point; an operating arm section connected to the remote joint and configured to fix a medical tool, rotate the tool about a remote rotation axis perpendicular to the reference straight-line and through the remote (Continued)

point, and move the tool in a direction perpendicular to the remote rotation axis and through the remote point; and an arm supporting section where the positioning arm section and the operating arm section are supported by connecting and the reference point is located.

15 Claims, 11 Drawing Sheets

(56) References Cited

U.S. PATENT DOCUMENTS

| | | | |
|---|---|---|---|
| 5,931,832 | A | 8/1999 | Jensen |
| 6,106,511 | A | 8/2000 | Jensen |
| 6,594,552 | B1 | 7/2003 | Nowlin et al. |
| 2006/0264915 | A1 | 11/2006 | Jensen |
| 2011/0022229 | A1 | 1/2011 | Jang et al. |
| 2012/0059392 | A1 | 3/2012 | Diolaiti |
| 2013/0325029 | A1 | 12/2013 | Hourtash et al. |
| 2013/0325031 | A1 | 12/2013 | Schena et al. |
| 2014/0296872 | A1 | 10/2014 | Cooper et al. |
| 2014/0371584 | A1 | 12/2014 | Cleary et al. |
| 2015/0342692 | A1 | 12/2015 | Yi et al. |
| 2016/0045272 | A1 | 2/2016 | Diolaiti |
| 2016/0252699 | A1 | 9/2016 | Yi et al. |
| 2016/0278871 | A1 | 9/2016 | Schena et al. |
| 2017/0056117 | A1 | 3/2017 | Hourtash et al. |
| 2017/0296277 | A1 | 10/2017 | Hourtash et al. |
| 2017/0299838 | A1 | 10/2017 | Yi et al. |
| 2019/0053863 | A1 | 2/2019 | Hongo et al. |
| 2019/0069965 | A1 | 3/2019 | Schena et al. |
| 2020/0016741 | A1 | 1/2020 | He et al. |
| 2020/0146763 | A1 | 5/2020 | Schena et al. |

FOREIGN PATENT DOCUMENTS

| | | |
|---|---|---|
| CN | 103930064 | 7/2014 |
| CN | 104334110 | 2/2015 |
| CN | 104349742 | 2/2015 |
| CN | 104622573 | 5/2015 |
| CN | 105832417 | 8/2016 |
| CN | 106618736 | 5/2017 |
| EP | 2 959 858 | 12/2015 |
| JP | 08-509886 | 10/1996 |
| JP | 2000-354986 | 12/2000 |
| JP | 2016-516453 | 6/2016 |
| KR | 10-2012-0014758 | 2/2012 |
| KR | 10-1307951 | 9/2013 |
| KR | 10-2014-0138540 | 12/2014 |
| KR | 10-2016-0122558 | 10/2016 |
| WO | 2010/026398 | 3/2010 |
| WO | 2017/120516 | 7/2017 |
| WO | 2017/077755 | 11/2017 |

OTHER PUBLICATIONS

International Search Report for International Application No. PCT/KR2018/010174, dated Feb. 1, 2019.
International Search Report for International Application No. PCT/KR2018/010180, dated Feb. 7, 2019.
Written Opinion for International Application No. PCT/KR2018/010174 with English translation, dated Feb. 1, 2019.
Written Opinion for International Application No. PCT/KR2018/010180 with English translation, dated Feb. 7, 2019.
Extended European search corresponding European Patent Application No. 18818971.6, dated Sep. 9, 2019.
Extended European search corresponding European Patent Application No. 18818970.8, dated Sep. 16, 2019.
Office Action from Intellectual Property of India corresponding to India Application No. 201817049104, dated Nov. 18, 2020.
Office Action from Intellectual Property of India corresponding to India Application No. 201817049106, dated Nov. 18, 2020.
Chinese Office Action, with English translation, corresponding to Chinese Application No. 201880002551.8, dated Jan. 6, 2021.

MEDICAL ARM ASSEMBLY

TECHNICAL FIELD

The present disclosure relates to a medical arm assembly. In particular, the present disclosure relates to a medical arm assembly configured to manipulate a medical tool.

This disclosure has been derived from research conducted as part of the WC300 Project Technology Development Support in Korea. [Task No. 52482672, Research Title: Development of navigation fusion head and neck surgery robot system with matching accuracy of 1 mm or less, Contribution rate: 1/1, Organizing institution: Koh Young Technology Co., Ltd., Research period: Mar. 1, 2017 to Dec. 31, 2021.

BACKGROUND

In general, a medical robot has a robot arm configured to operate a medical tool such as a surgical tool or an endoscope. A medical tool is mounted on the fore-end of the robot arm, and the tool also moves in accordance with the movement of the robot arm, so that an operation can be performed.

The robot arm includes a plurality of links configured to be movable relative to each other. The plurality of links may be connected through joints such as hinges. One of two links connected to each other by a joint is movable relative to the other. The robot arm includes a motor that provides a driving force such that the multiple links are movable relative to each other.

SUMMARY

In the process of performing surgery by perforating a portion of a patient's skin and inserting a tool therein, unnecessary damage to the skin of the human body may occur due to the movement of the robot arm of the related art. In addition, when the surgical site is wide, there is a disadvantage in that it is necessary to make a relatively wide incision in the skin or to perforate the skin at multiple respective operation sites in order to secure a path through which the tool is movable. Embodiments of the present disclosure may overcome this disadvantage by allowing the tool to rotate about a virtual center of rotation (remote point) of the fore-end of the robotic arm.

The situation may arise in which it is necessary to change the aforementioned remote point of the robot arm according to the needs of a user (e.g., a doctor). Embodiments of the present disclosure provide technology by which the position of the above-mentioned remote point can easily be changed and fixed to a desired position.

The present disclosure provides embodiments of a medical arm assembly. A medical arm assembly according to an embodiment of the present disclosure includes: a remote joint in which a remote point spaced apart from a reference point is located; a positioning arm section configured to support the remote joint, move the remote joint such that the relative position of the remote point with respect to the reference point is changed only in the direction of a virtual reference straight line passing through the reference point and the remote point, and fix the relative position of the remote point with respect to the reference point; an operating arm section connected to the remote joint, the operating arm section being configured to fix a medical tool thereto and rotate the tool about a remote rotation axis that is perpendicular to the reference straight line and that passes through the remote point, the operating arm section being configured to move the tool in a direction that is perpendicular to the remote rotation axis and that passes through the remote point; and an arm supporting section to which the positioning arm section and the operating arm section are connected to be supported, the reference point being located in the arm supporting section.

In an embodiment, the arm supporting section may be configured to be rotatable about the reference straight line.

In an embodiment, the medical arm assembly may further include an arm supporting section motor configured to provide driving force for rotating the arm supporting section about the reference straight line.

In an embodiment, the positioning arm section may include a positioning motor configured to provide driving force so as to change the relative position of the remote point.

In an embodiment, the operating arm section may include an ending link slidably supported on the remote joint, and the positioning arm section may include a guide link connected to the remote joint.

In an embodiment, the ending link may be configured to be rotatable about the remote rotation axis and to be movable in a direction that is perpendicular to the remote rotation axis and that passes through the remote point.

In an embodiment, the remote joint may include a sliding part configured to slidably support the ending link, and a hinge part configured to rotatably connect the guide link to the sliding part.

In an embodiment, the operating arm section may include: an ending link slidably supported on the remote joint; a middle link connected to the ending link so as to be rotatable about a rotation axis parallel to the remote rotation axis; and a starting link connected to the middle link so as to be rotatable about a rotation axis parallel to the remote rotation axis, and connected to the arm supporting section so as to be rotatable about a rotation axis parallel to the remote rotation axis.

In an embodiment, the operating arm section may further include: a first counterweight configured to provide a gravity load such that a connection point between the starting link and the middle link is lifted upwards; and a second counterweight configured to provide a gravity load such that a connection point between the middle link and the ending link is lifted upwards.

In an embodiment, the operating arm section may further include: a first operating motor configured to provide driving force for rotating the starting link with respect to the arm supporting section; and a second operating motor, configured to provide driving force for rotating the middle link with respect to the starting link.

In an embodiment, the operating arm section may further include: a first link connected to the arm supporting section so as to be rotatable about a rotation axis parallel to the remote rotation axis; and a second link connected to the first link so as to be rotatable about a rotation axis parallel to the remote rotation axis, and connected to the middle link so as to be rotatable about a rotation axis parallel to the remote rotation axis. With reference to the connection point between the middle link and the starting link, a connection point between the middle link and the second link may be located on an opposite side of a connection point between the middle link and the ending link.

In an embodiment, the positioning arm section may include a guide link, which is connected to the remote joint and is connected to the arm supporting section so as to be movable in the direction of the reference straight line.

In an embodiment, the positioning arm section may include: a guide link connected to the remote joint; and a rotating link connected to the guide link so as to be rotatable about a guide rotation axis, and connected to the arm supporting section so as to be rotatable about a rotation axis parallel to the guide rotation axis.

In an embodiment, the positioning arm section may further include: a sliding link, which is connected to the arm supporting section so as to be movable in a direction perpendicular to the guide rotation axis and is connected to the guide link so as to be rotatable about a rotation axis parallel to the guide rotation axis. With reference to a connection point between the guide link and the rotating link, a connection point between the guide link and the sliding link may be located on an opposite side of the remote joint.

In an embodiment, the positioning arm section may further include: a first operating link connected to the arm supporting section so as to be rotatable about a rotation axis parallel to the guide rotation axis; and a second operating link connected to the first operating link so as to be rotatable about a rotation axis parallel to the guide rotation axis and connected to the guide link so as to be rotatable about a rotation axis parallel to the guide rotation axis. With reference to a connection point between the guide link and the rotating link, a connection point between the guide link and the second operating link may be located on an opposite side of the remote joint.

According to embodiments of the present disclosure, a medical tool can be operated with various motions while minimizing the size of a perforation area for surgery in the user's skin.

According to embodiments of the present disclosure, it is possible to easily adjust the position of a remote point of the medical arm assembly and fix the position thereof, thereby allowing the user to conveniently perform preparation for surgery and to easily adapt to changes in the circumstances.

DETAILED DESCRIPTION

Figure 1:
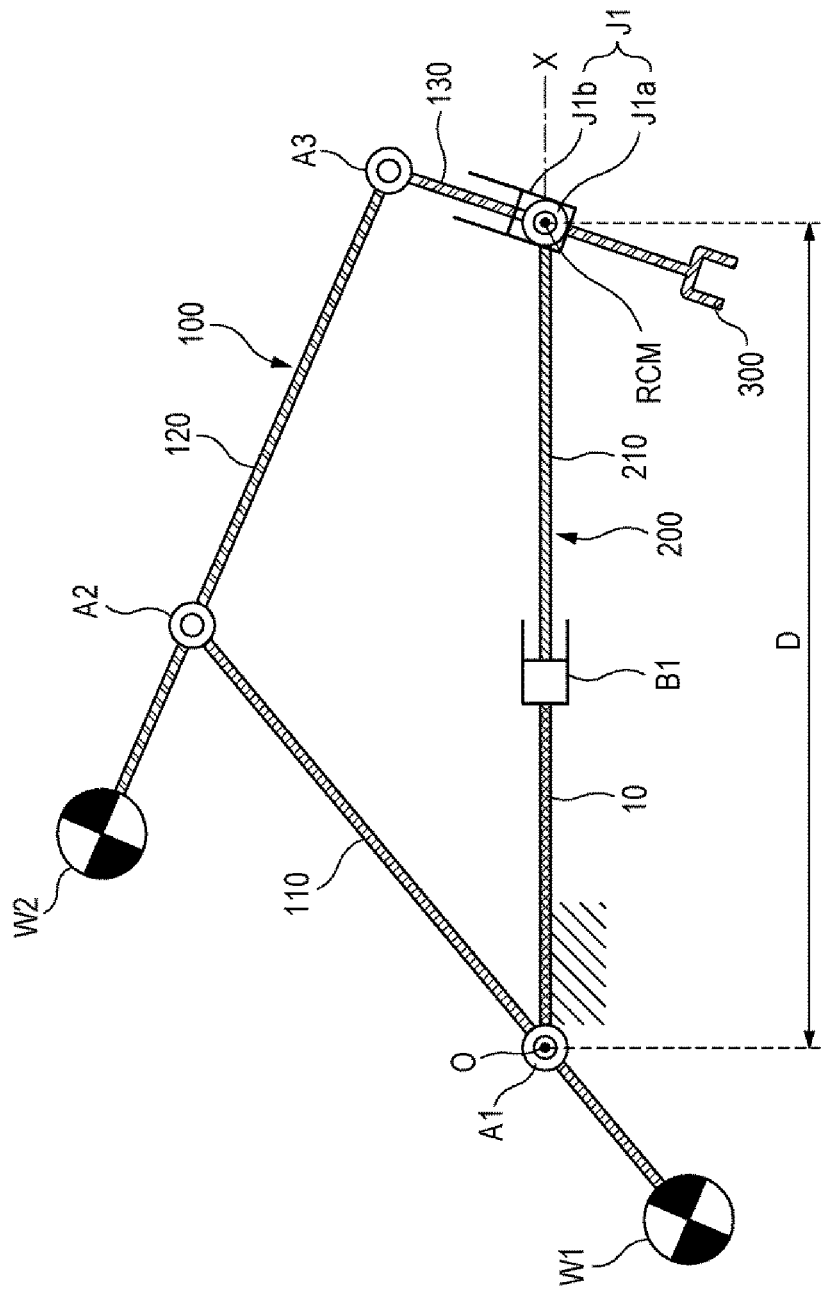
FIG. 1 is a conceptual elevation illustrating some mechanism of a medical arm assembly according to an embodiment of the present disclosure.

Embodiments of the present disclosure are exemplified for the purpose of describing the technical idea of the present disclosure. The scope of the present disclosure is not limited to the embodiments illustrated below or to the detailed description of the embodiments.

All technical and scientific terms used in the present disclosure have meanings commonly understood by a person ordinarily skilled in the art to which the present disclosure belongs unless otherwise defined. All the terms used in the present disclosure are selected for the purpose of more clearly describing the present disclosure, and are not selected to limit the scope of the present disclosure.

As used in this disclosure, terms such as "including", "comprising," and "having" should be understood as open-ended terms that imply the possibility of including other embodiments unless otherwise mentioned in the phrase or sentence in which the terms are contained.

A singular term used in the present disclosure may include the plural meaning thereof unless otherwise mentioned, which is equally applicable to a singular term set forth in the claims.

Terms such as "first" and "second" are used in order to distinguish a plurality of components from one another, and do not limit the order or importance of the corresponding components.

Direction-indicating terms, such as "forward" used in the present disclosure, indicate a direction based on the direction in which a remote point RCM is located with respect to a reference point O in the accompanying drawings, and direction-indicating terms such as "rearward" indicate the direction opposite thereto. Direction-indicating terms such as "upward" and "upper" used in the present disclosure indicate the direction in which a middle link 130 is located with respect to a reference straight line X in the accompanying drawings, and direction-indicating terms such as "downward" and "lower" indicate a direction opposite thereto. The reference point O, the remote point RCM, the reference straight line X, and the middle link 130 shown in the accompanying drawings may be oriented differently, and the direction-indicating terms may be interpreted accordingly.

Hereinafter, embodiments of the present disclosure will be described with reference to the accompanying drawings. In the accompanying drawings, the same or corresponding components are denoted by the same reference numerals. In the following description of the embodiments, duplicate descriptions of the same or corresponding components may be omitted. However, even if the descriptions of components are omitted, such components are not intended to be excluded from any embodiment.

A medical arm assembly according to an embodiment of the present disclosure may be used as a single-port surgery robot. Here, the term "single-port surgery" refers to a surgical operation in which a medical tool is inserted through a single perforation site of a patient, and the perforation site may be an incision site or an existing orifice such as a mouth. For example, the medical arm assembly according to an embodiment of the present disclosure may be applied to a robot that performs laryngeal surgery via the throat or a robot for an endoscope.

FIG. 1 is a conceptual elevation illustrating some mechanism of a medical arm assembly according to an embodiment of the present disclosure. In FIG. 1, a support joint J0 and a platform 20, to be described later, which are connected to an arm supporting section 10, are omitted, unlike the other drawings.

The medical arm assembly may include a remote joint J1 where a remote point RCM spaced apart from a reference point O is located. The reference point O means a virtual point disposed at a fixed position of the medical arm assembly. The remote point RCM is a virtual point located in the remote joint J1 and moves together with the remote joint J1 when the remote joint J1 moves. The remote point RCM may be referred to as a "remote center" or a "RCM (Remote Center of Motion)".

The medical arm assembly may include a positioning arm section 200 configured to support the remote joint J1. The positioning arm section 200 may be supported by the arm supporting section 10.

The positioning arm section 200 may include a guide link 210, one end of which is connected to the remote joint J1. The guide link 210 may be connected to a hinge part J1a of the remote joint J1.

The positioning arm section 200 may be configured to move the remote joints J1 such that the relative position of the remote point RCM with respect to the reference point O is changed only in the direction of a virtual reference straight line X passing through the reference point O and the remote point RCM. For example, the guide link 210 of the positioning arm section 200 may be connected to the arm supporting section 10 so as to be slidable in the direction of the reference axis X. By the joint B1, the guide link 210 may be slidably connected to the arm supporting section 10.

The positioning arm section 200 may be configured to fix the relative position of the remote point RCM with respect to the reference point O. For example, the guide link 210 of the positioning arm section 200 may be fixed to the arm supporting section 10 by the brake.

Through this, the user may move the positioning arm section 200 such that the remote point RCM is disposed at a desired position on the reference straight line X, and may then fix the position of the remote point RCM using the brake. For example, when the guide link 210 having 1 degree of freedom (1-DOF) is slid by the joint B1 in the direction of the reference straight line X, the distance D of the remote point RCM to the reference point O can be changed. After the distance D is changed, when the joint B1 fixes the guide link 210 so as to prevent the same from sliding using the brake, the distance D can be maintained constant.

The medical arm assembly may include an operating arm section 100 connected to the remote joint J1. The operating arm section 100 may be supported by the arm supporting section 10. The operating arm section portion 100 may be supported by the arm supporting section 10 and the remote joint J1.

The operating arm section 100 may be configured to fix a medical tool 300 thereto. For example, the medical tool may be a surgical tool or an endoscope. The tool 300 may also be referred to as an end effector. The tool 300 may be fixed to a distal end of the operating arm section 100. The tool 300 may be fixed to the lower end of an ending link 130 of the operating arm section 100.

The operating arm section 100 may be configured to rotate the tool 300 around a remote rotation axis. Here, the remote rotation axis means a virtual rotation axis that is perpendicular to the reference straight line X and that passes through the remote point RCM. For example, when a starting link 110 of the operating arm section 100 rotates about the joint A1, the ending link 130 of the operating arm section 100 is rotated about the hinge part J1a, and the tool 300 is rotated integrally with the ending link 130.

The "rotation axis" referred to in this disclosure is a virtual axis for describing the present disclosure, and does not mean an actual component of an apparatus. As an example, in order to provide the function of the rotation axis, a shaft disposed on the rotation axis may be provided. As another example, in order to provide the function of the rotation axis, a protrusion protruding along the rotation axis may be provided on one of the two components and a recess may be provided on the remaining one of the two components such that the protrusion is rotatably engaged with the recess.

The operating arm section 100 may be configured to move the tool 300 in a direction that is perpendicular to the remote rotation axis and passes through the remote point. Here, the direction that is perpendicular to the remote rotation axis and passes through the remote point may be a direction that is not parallel to the reference straight line X. For example, when the middle link 120 of the operating arm section 100 rotates about the joint A2, the ending link 130 of the operating arm section 100 is moved by a sliding part J1b of the remote joint J1 in a direction that is perpendicular to the remote rotation axis and passes through the remote point, and the tool 300 may be moved integrally with the ending link 130.

In this specification, the wording "a first component and a second component rotate integrally" means that the first component rotates in the same direction of rotation as the second component at the same rotating speed as the second component. In this specification, the wording "a first component and a second component move integrally" means that the first component moves in the same direction as the second component at the same speed as the second component.

The medical arm assembly may include an arm supporting section 10 to which the positioning arm section 200 and the operating arm section 100 are connected so as to be supported. For example, the operating arm section 100 is connected to and supported by the arm supporting section 10 by the joint A1, and the positioning arm section 200 is connected to the arm supporting section 10 by the joint B1.

The reference point O may be located on the arm supporting section 10. For example, the reference point O may be located in the joint A1.

The remote joint J1 may include a sliding part J1b on which the ending link 130 is slidably supported. The sliding part J1b may guide the ending link 130 such that the ending link 130 is slidable in a direction that is perpendicular to the remote rotation axis and passes through the remote point.

The remote joint J1 may include a hinge part J1a that rotatably connects the guide link 210 to the sliding part Jib. The hinge part J1a is capable of making the ending link 130 rotatable about the remote rotation axis.

The medical arm assembly may include counterweights W1 and W2 for balancing a gravity load. The medical arm assembly may include a first counterweight W1 and a second counterweight W2.

Figure 2:
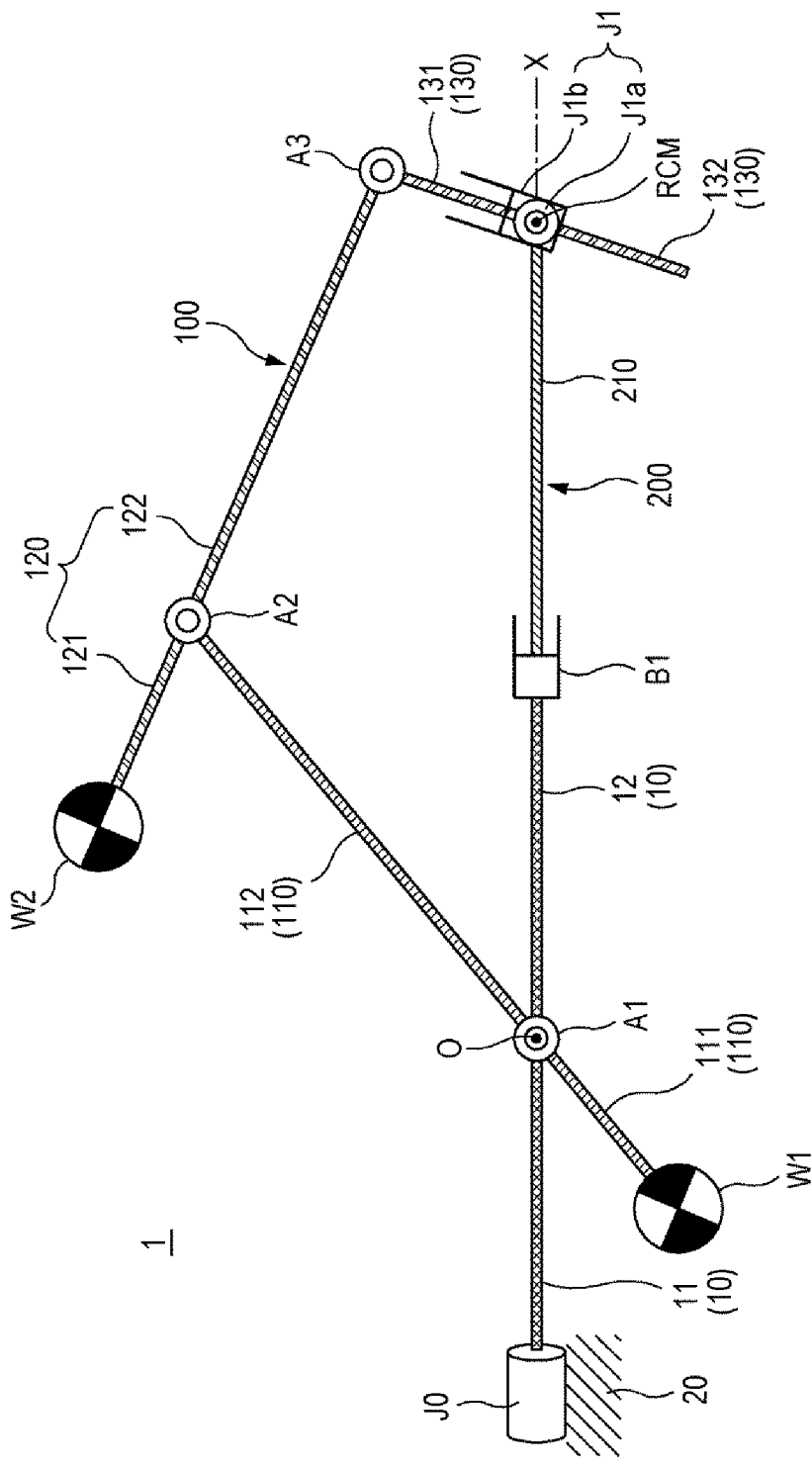
FIG. 2 is a conceptual elevation illustrating a medical arm assembly 1 according to a first embodiment of the present disclosure.

FIG. 2 is a conceptual elevation illustrating a medical arm assembly 1 according to a first embodiment of the present disclosure. The description of the medical arm assembly according to the embodiment described above with reference to FIG. 1 is also applicable to a medical arm assembly 1 according to the first embodiment to be described later.

In the first embodiment, the tool 300 is capable of performing a 3-DOF motion in the state in which the remote point RCM is fixed. Specifically, in the state in which the remote point RCM is fixed, the tool 300 is 1) rotatable about the remote rotation axis, 2) movable in a direction that is perpendicular to the remote rotation axis and passes through the remote point RCM, and 3) rotatable about the reference straight line X. This 3-DOF motion may be possible in the state in which the position of the remote point RCM is fixed. Thus, when the remote point RCM is located at a perforation site of the patient, it is possible to freely operate the tool while minimizing the size of the perforation site.

In the first embodiment, when a motion of changing the remote point RCM by the positioning arm section 200 is added to the 3-DOF motion, the tool is capable of performing a 4-DOF motion. Through this 4-DOF motion, when it is necessary to locate the remote point RCM at a perforation site of a patient for preparation of surgery or when it is necessary to locate the remote point RCM at another perforation site during the surgery, convenience of manipulation of the medical arm assembly is improved.

The assembly of the arm supporting section 10 and the operating arm section 100 in the medical arm assembly 1 according to the first embodiment includes a 3-DOF serial arm. The positioning arm section 200 of the medical arm assembly 1 is configured to have a brake function and to perform a 1-DOF linear motion. In the first embodiment, the brake function is capable of being performed by restricting the movement of the guide link 210 in the direction of the reference straight line X at the joint B1. In the medical arm assembly 1, a support joint J0, a joint A1, a joint A2, and a joint B1 are independent joints, and a joint A3 and the remote joint J1 are dependent joints. In the present disclosure, an "independent joint" means a joint whose operation is directly controlled by the driving force of a motor, and a "dependent joint" means a joint whose operation is passively operated by the operation of the independent joint.

The arm supporting section 10 of the medical arm assembly 1 may be elongated along the reference straight line X. The joint A1 may be disposed in the middle of the arm supporting section 10 of the medical arm assembly 1. The arm supporting section 10 of the medical arm assembly 1 may include a forward end portion 12 and a rearward end portion 11 with respect to the joint A1. The support joint J0 may be connected to the rearward end portion 11. The joint B1 may be connected to the forward end portion 12.

The arm supporting section 10 of the medical arm assembly 1 may be configured to be rotatable about the reference straight line X. The arm supporting section portion 10 is rotatable about the reference straight line X with respect to the platform 20 by the support joint J0. When the arm supporting section 10 rotates about the reference straight line X, the operating arm section 100 and the positioning arm section 200 rotate about the reference straight line X integrally with the arm supporting section 10. Accordingly, the tool fixed to the operating arm section 100 is capable of rotating about the reference straight line X.

The medical arm assembly 1 may include an arm supporting section motor (not shown) for providing driving force for rotating the arm supporting section 10 about the reference straight line X. The support joint J0 is capable of rotating the arm supporting section 10 using the arm supporting section motor.

The medical arm assembly 1 may include the platform 20 that supports the arm supporting section 10. The support joint J0 may be connected to the platform 20. In an example, the platform 20 may fixedly support the support joint J0. In another example, the platform 20 is capable of supporting the support joint J0 such that the platform 20 is positionally movable in at least one of the upward-and-downward direction, the forward-and-rearward direction, and the left-and-right direction.

The operating arm section 100 of the medical arm assembly 1 includes an ending link 130 slidably supported by the remote joint J1. The ending link 130 is configured to be movable in a direction perpendicular to the remote rotation axis and passing through the remote point RCM. The ending link 130 may be slidably supported by the sliding part J1b of the remote joint J1.

The ending link 130 of the medical arm assembly 1 is configured to be rotatable about the remote rotation axis. The ending link 130 may be rotatably supported by the hinge part J1a of the remote joint J1.

The ending link 130 of the medical arm assembly 1 extends through the remote point RCM. The ending link 130 includes a lower end portion 132 and an upper end portion 131. The tool 300 is fixed to the lower end portion 132. The upper end portion 131 is connected to the joint A3.

The operating arm section 100 of the medical arm assembly 1 includes a middle link 120 connected to the ending link 130 so as to be rotatable about a rotation axis parallel to the remote rotation axis. The middle link 120 is connected to the ending link 130 by the joint A3. The joint A3 includes a hinge having a rotation axis parallel to the remote rotation axis.

The joint A2 is disposed in the middle link 120 of the medical arm assembly 1. The middle link 120 includes a forward end portion 122 and a rearward end portion 121 with respect to the joint A2. The forward end portion 122 of the middle link 120 is connected to the joint A3. The forward end portion 122 of the middle link 120 is rotatably connected to the upper end portion 131 of the ending link 130. The second counterweight W2 is fixed to the rearward end portion 121 of the middle link 120.

The operating arm section 100 of the medical arm assembly 1 includes a starting link 110 connected to the middle link so as to be rotatable about a rotation axis parallel to the remote rotation axis. The starting link 110 is connected to the middle link 120 by the joint A2. The joint A2 includes a hinge having a rotation axis parallel to the remote rotation axis.

The starting link 110 of the medical arm assembly 1 is connected to the arm supporting section 10 so as to be rotatable about a rotation axis parallel to the remote rotation axis. The starting link 110 is connected to the arm supporting section 10 by the joint A1. The joint A1 includes a hinge having a rotation axis parallel to the remote rotation axis.

The joint A1 is disposed in the starting link 110 of the medical arm assembly 1. The starting link 110 includes an upper portion 112 and a lower portion 111 with respect to the joint A1. The upper end portion 112 of the starting link 110 is connected to the joint A2. The first counterweight W1 is fixed to the lower end portion 111 of the starting link 110.

The first counterweight W1 provides a gravity load such that a connection point between the starting link 110 and the middle link 120 (the point where the joint A2 is located) is lifted upwards. The first counterweight W1 may be fixed to the starting link 110. The first counterweight W1 is disposed on an opposite side of the connection point between the starting link 110 and the middle link 120 (the point where the joint A2 is located) with respect to the connection point between the starting link 110 and the arm supporting section 10 (the point where the joint A1 is located).

The second counterweight W2 provides a gravity load such that a connection point between the middle link 120 and the ending link 130 (the point where the joint A3 is located) is lifted upwards. The second counterweight W2 may be fixed to the middle link 120. The second counterweight W2 is disposed on an opposite side of the connection point between the middle link 120 and the ending link 130 (the point where the joint A3 is located) with respect to the connection point between the starting link 110 and the middle link 120 (the point where the joint A2 is located).

The operating arm section 100 of the medical arm assembly 1 includes a first operating motor (not shown) that provides a driving force for rotating the starting link 110 with respect to the arm supporting section 10. The joint A1 is capable of rotating the starting link 110 with respect to the arm supporting section 10 by the first operating motor.

The operating arm section 100 of the medical arm assembly 1 includes a second operating motor (not shown) that provides driving force for rotating the middle link 120 with respect to the starting link 110. The joint A2 is capable of rotating the middle link 120 with respect to the starting link 110 by the second operating motor.

The positioning arm section 200 of the medical arm assembly 1 includes a guide link 210 connected to the remote joint J1. The guide link 210 may be connected to the hinge part J1a of the remote joint J1 at one end thereof.

The guide link 210 of the medical arm assembly 1 is connected to the arm supporting section 10 so as to be movable in the direction of the reference straight line X. The guide link 210 is connected to the arm supporting section 10 by the joint B1. The joint B1 includes a guide configured to guide the movement of the guide link 210 in the direction of the reference straight line X.

The positioning arm section 200 includes a positioning motor (not shown) so as to provide driving force to change the relative position of the remote point RCM. The position of the remote joint J1 is capable of being changed using only one positioning motor. The joint B1 is capable of moving the guide link 210 in the direction of the reference straight line X with respect to the arm supporting section 10 using the positioning motor.

Figure 3:
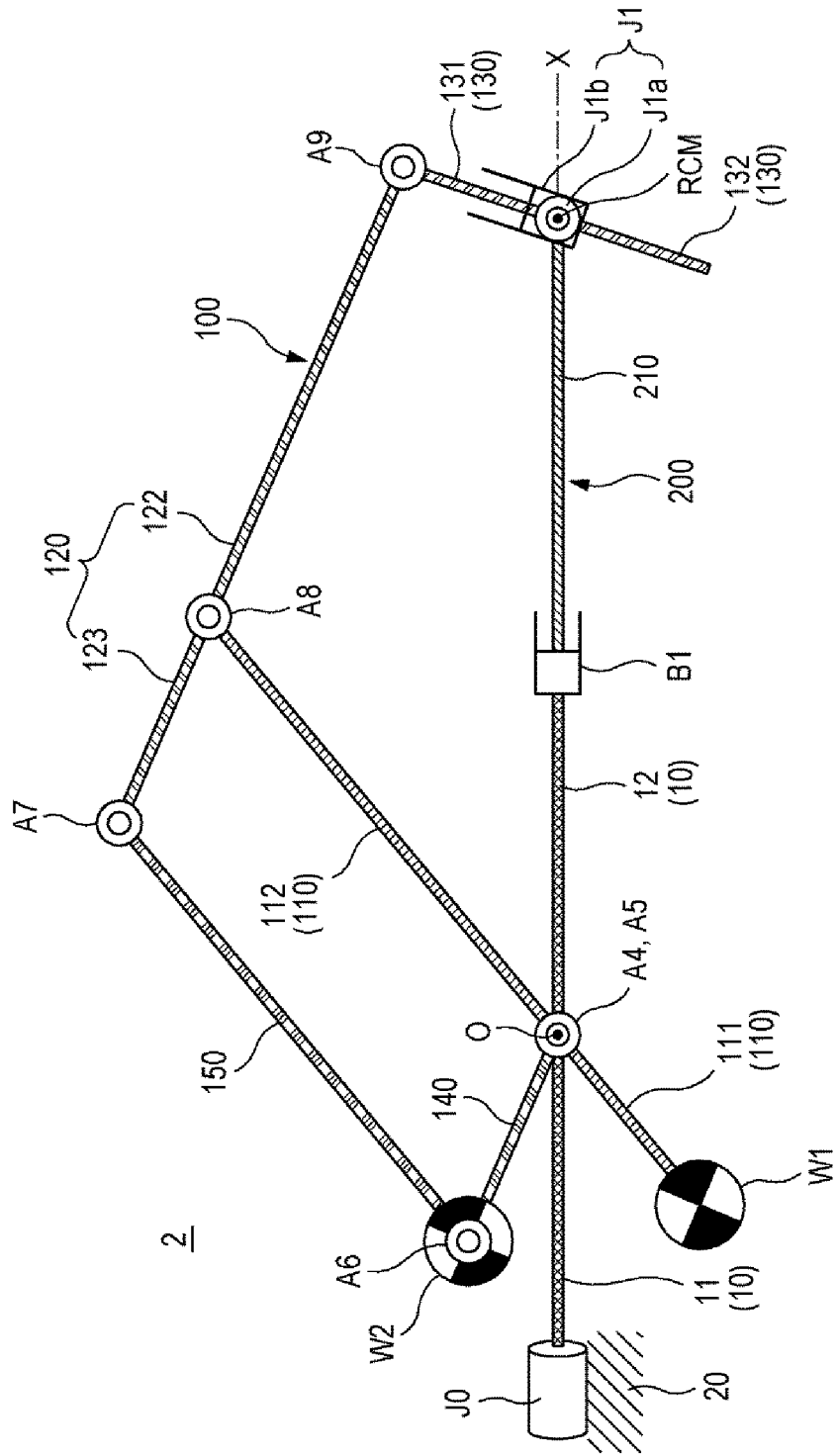
FIG. 3 is a conceptual elevation illustrating a medical arm assembly 2 according to a second embodiment of the present disclosure.

FIG. 3 is a conceptual elevation illustrating a medical arm assembly 2 according to a second embodiment of the present disclosure. The positioning arm section 200 of the medical arm assembly 2 according to the second embodiment is the same as the positioning arm section 200 according to the first embodiment described above, and thus a description thereof will be omitted. Hereinafter, referring to FIG. 3, the medical arm assembly 1 according to the second embodiment will be described, focusing on differences from the first embodiment.

The assembly of the arm supporting section 10 and the operating arm section 100 in the medical arm assembly 2 according to the second embodiment has 3 DOF and includes five bars. The positioning arm section 200 of the medical arm assembly 2 is configured to have a brake function and to perform a 1-DOF linear motion. In the medical arm assembly 2, a joint J0, a support joint A4, a joint A5, and a joint B1 are independent joints, and a joint A6, a joint A7, a joint A8, a joint A9, and a remote joint J1 are dependent joints.

The joint A4 and the joint A5 may be disposed in the middle of the arm supporting section 10 of the medical arm assembly 2. The arm supporting section 10 of the medical arm assembly 2 includes a forward end portion 12 and a rearward end portion 11 with respect to the joint A4 and the joint A5.

The upper end portion 131 of the ending link 130 of the medical arm assembly 2 is connected to the joint A9. The middle link 120 is connected to the ending link 130 by the joint A9. The joint A9 includes a hinge having a rotation axis parallel to the remote rotation axis.

The joint A8 is disposed in the middle link 120 of the medical arm assembly 2. The middle link 120 includes a forward end portion 122 and a rearward end portion 123 with respect to the joint A8. The forward end portion 122 of the middle link 120 is connected to the joint A9. The forward end portion 122 of the middle link 120 is rotatably connected to the upper end portion 131 of the ending link 130. The rearward end portion 123 of the middle link 120 is connected to the joint A7. The rearward end portion 123 of the middle link 120 is rotatably connected to a second link 150.

The starting link 110 of the medical arm assembly 2 is connected to the middle link 120 by the joint A8. The joint A8 includes a hinge having a rotation axis parallel to the remote rotation axis.

The starting link 110 of the medical arm assembly 2 is connected to the middle link 10 by the joint A4. The joint A4 includes a hinge having a rotation axis parallel to the remote rotation axis.

The joint A4 is disposed in the starting link 110 of the medical arm assembly 2. The starting link 110 includes an upper portion 112 and a lower portion 111 with respect to the joint A4. The upper end portion 112 of the starting link 110 is connected to the joint A8. The first counterweight W1 is fixed to the lower end portion 111 of the starting link 110.

The operating arm section 100 of the medical arm assembly 2 further includes a first link 140 connected to the arm supporting section 10 so as to be rotatable about a rotation axis parallel to the remote rotation axis. The first link 140 is connected to the second link 150 so as to be rotatable about a rotation axis parallel to the remote rotation axis.

One end of the first link 140 of the medical arm assembly 2 is connected to the joint A5, and the other end is connected to the joint A6. The first link 140 is connected to the arm supporting section 10 by the joint A5. The joint A5 includes a hinge having a rotation axis parallel to the remote rotation axis. The first link 140 is connected to the second link 150 by the joint A6. The joint A6 includes a hinge having a rotation axis parallel to the remote rotation axis.

The operating arm section 100 of the medical arm assembly 2 further includes a second link 150 connected to the first link 140 so as to be rotatable about a rotation axis parallel to the remote rotation axis. The second link 150 is connected to the middle link 120 so as to be rotatable about a rotation axis parallel to the remote rotation axis.

One end of the second link 150 of the medical arm assembly 2 is connected to the joint A6, and the other end is connected to the joint A7. The second link 150 is connected to the first link 140 by the joint A6. The second link 150 is connected to the middle link 120 by the joint A7. The joint A7 includes a hinge having a rotation axis parallel to the remote rotation axis.

With reference to the connection point between the middle link 120 and the starting link 110 of the medical arm assembly 2 (the point where the joint A8 is located), the connection point between the middle link 120 and the second link 150 (the point where the joint A7 is located) is located on an opposite side of the connection point between the middle link 120 and the ending link 130 (the point where the joint A9 is located). With reference to the joint A8, the joint A9 may be located at the forward side and the joint A7 may be located at the rearward side. The joint A6 is located behind the joint A7 and the joint A5.

The first counterweight W1 of the medical arm assembly 2 is disposed on an opposite side of the connection point between the starting link 110 and the middle link 120 (the point where the joint A8 is located) with respect to the connection point between the starting link 110 and the arm supporting section 10 (the point where the joint A4 is located).

The second counterweight W2 of the medical arm assembly 2 may be fixed to the joint A6. The second counterweight W2 may be disposed behind the joint A7.

The joint A4 is capable of rotating the starting link 110 with respect to the arm supporting section 10 by the first operating motor (not shown) of the medical arm assembly 2. The joint A5 is capable of rotating the first link 140 with respect to the arm supporting section 10 by the second operating motor (not shown) of the medical arm assembly 2.

Figure 4:
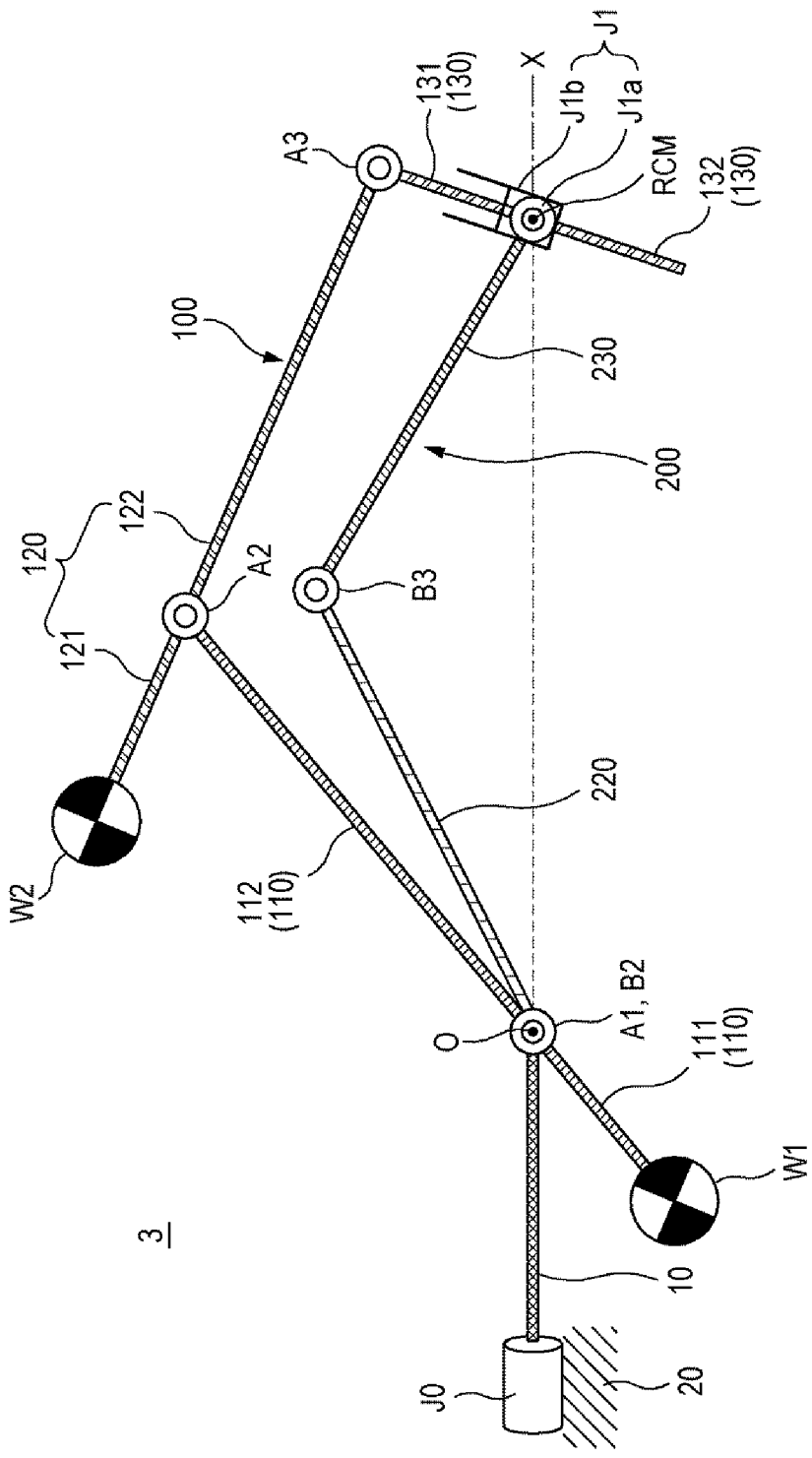
FIG. 4 is a conceptual elevation illustrating a medical arm assembly 3 according to a third embodiment of the present disclosure.

FIG. 4 is a conceptual elevation illustrating a medical arm assembly 3 according to a third embodiment of the present disclosure. The operating arm section 100 of the medical arm assembly 3 according to the third embodiment is the same as the operating arm section 100 according to the first embodiment described above, and a description thereof will thus be omitted. Hereinafter, referring to FIG. 4, the medical arm assembly 3 according to the third embodiment will be described, focusing on differences from the first embodiment.

The assembly of the arm supporting section 10 and the operating arm section 100 in the medical arm assembly 3 according to the third embodiment includes a 3-DOF serial arm. In the third embodiment, the brake function is capable of being performed by restricting the rotation of the rotating link 220 at the joint B2. In the medical arm assembly 3, a support joint J0, a joint A1, and a joint A2 are independent joints, and a joint A3 and a remote joint J1 are dependent joints.

Further, one of the joint B2 and the joint B3 is an independent joint and the other is a dependent joint. In an embodiment, the joint B2 is an independent joint, and the joint B3 is a dependent joint that is passively operated by the operation of the joint B2. In an example, the rotation of the joint B2 may be set to be performed in accordance with the rotation of the joint B3 through a belt and a pulley. In another example, the rotation of the joint B2 may be set to be performed in accordance with the rotation of the joint B3 through a plurality of gears, such as a bevel gear and a spur gear.

When the joint B2 rotates the rotating link 220 in the specific rotation direction and at a specific rotating speed with respect to the arm supporting section 10, at the joint B3, the guide link 230 may be set to rotate in an opposite direction of the specific rotation direction and at the same rotating speed as the specific rotating speed with respect to the rotating link 220. Thereby, the remote point RCM becomes movable only on one reference straight line X. Here, the rotating link 220 and the guide link 230 may have the same length. The distance between the joint B2 and the joint B3 may be equal to the distance between the joint B3 and the remote joint J1. This allows the remote point RCM to linearly move in the direction of the reference straight line X in accordance with the operation of the rotating link 220 and the guide link 230, which perform motions dependent on each other. After the remote point RCM is changed, the position of the remote point RCM is capable of being fixed by braking the joint B2.

The joint A1 and the joint B2 may be disposed at the distal end of the arm supporting section 10 of the medical arm assembly 3. The support joint J0 may be connected to the rearward end of the arm supporting section 10 of the medical arm assembly 3, and the joint A1 and the joint B2 may be connected to the forward end of the arm supporting section 10.

The positioning arm section 200 of the medical arm assembly 3 includes a guide link 230 connected to the remote joint J1. The guide link 230 may be connected to the hinge part J1a of the remote joint J1 at one end thereof.

The guide link 230 of the medical arm assembly 3 is connected to the rotating link 220 so as to be rotatable about a guide rotation axis. The guide link 230 is connected to the rotating link 220 by the joint B3. The joint B3 includes a hinge having the guide rotation axis. The guide rotation axis may extend in a direction perpendicular to the reference axis X. The guide rotation axis may be parallel to the remote rotation axis.

The positioning arm section 200 of the medical arm assembly 3 includes the rotating link 220 connected to the guide link 230 so as to be rotatable about the guide rotation axis. The rotating link 220 is connected to the arm supporting section 10 so as to be rotatable about a rotation axis parallel to the remote rotation axis. The rotating link 220 is connected to the arm supporting section 10 by the joint B2. The joint B2 includes a hinge having a rotation axis parallel to the guide rotation axis.

The joint B2 is capable of rotating the rotating link 220 with respect to the arm supporting section 10 using only one positioning motor of the medical arm assembly 3, and the joint B3 is capable of rotating the guide link 230 with respect to the rotating link 220.

Figure 5:
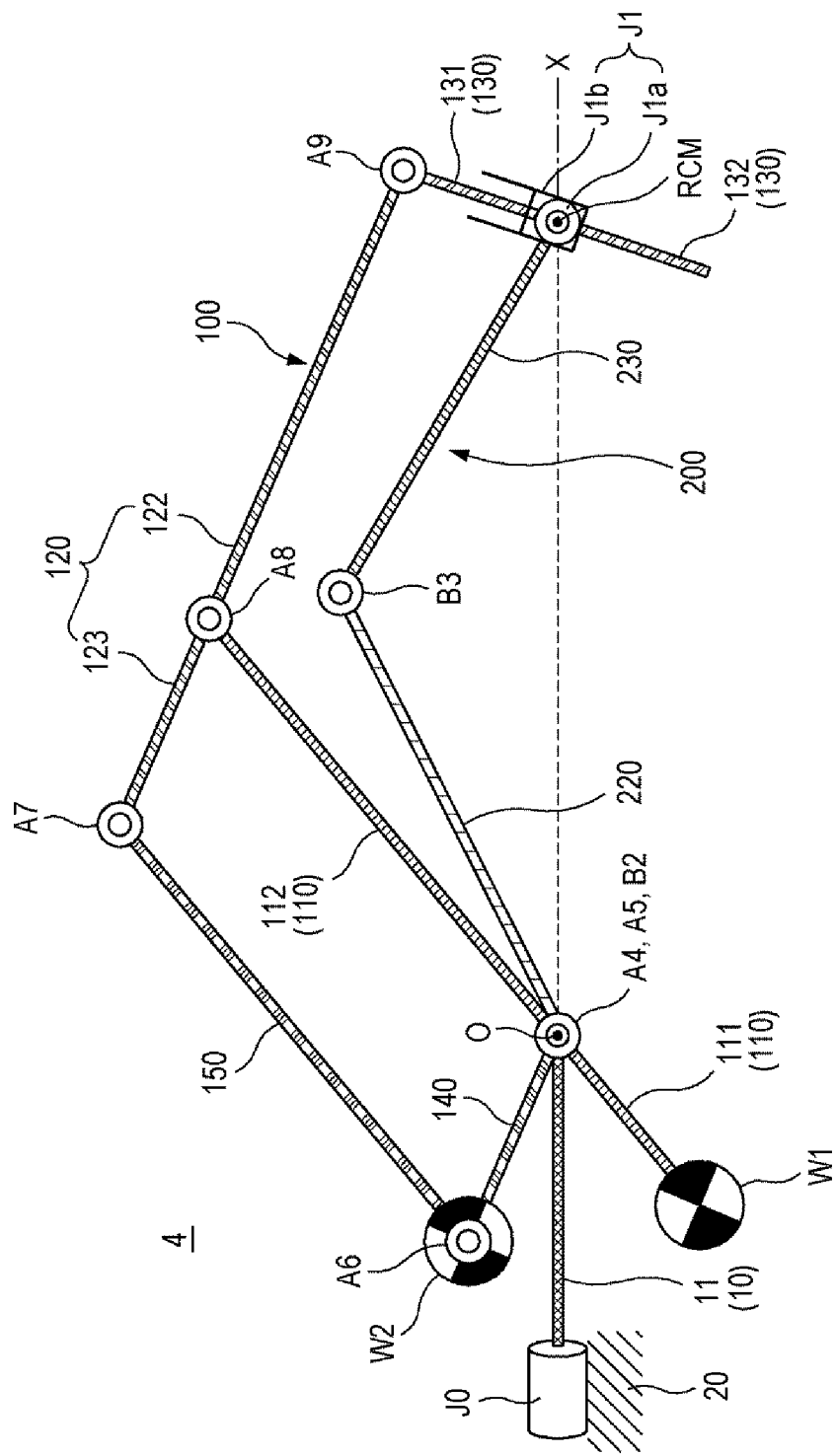
FIG. 5 is a conceptual elevation illustrating a medical arm assembly 4 according to a fourth embodiment of the present disclosure.

FIG. 5 is a conceptual elevation illustrating a medical arm assembly 4 according to a fourth embodiment of the present disclosure. The operating arm section 100 of the medical arm assembly 3 according to the fourth embodiment is the same as the operating arm section 100 according to the second embodiment described above, and a description thereof will thus be omitted. The positioning arm section 200 of the medical arm assembly 4 according to the fourth embodiment is the same as the positioning arm section 200 according to the third embodiment described above, and a description thereof will thus be omitted.

Figure 6:
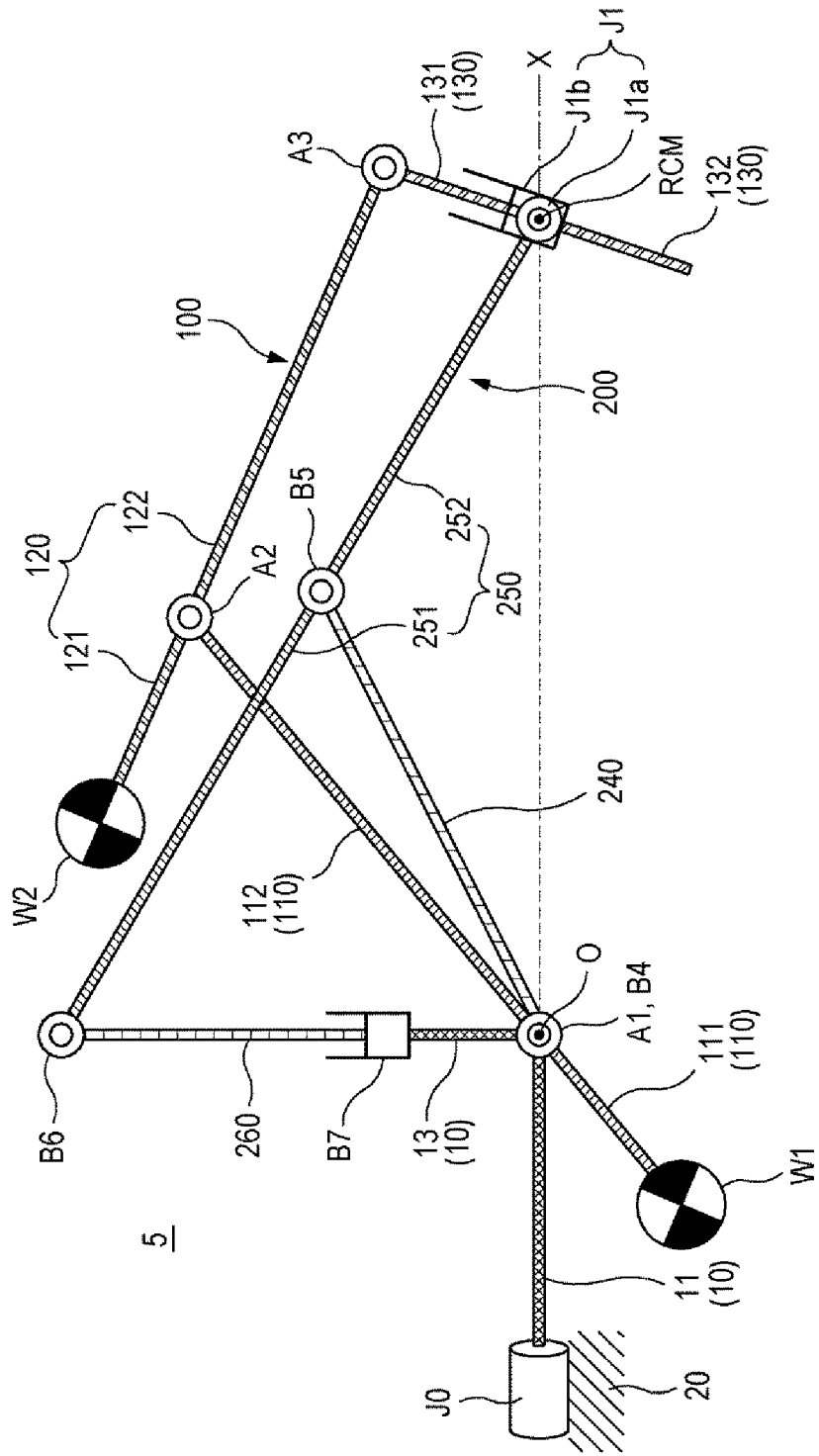
FIG. 6 is a conceptual elevation illustrating a medical arm assembly 5 according to a fifth embodiment of the present disclosure.

FIG. 6 is a conceptual elevation illustrating a medical arm assembly 5 according to a fifth embodiment of the present disclosure. The operating arm section 100 of the medical arm assembly 5 according to the fifth embodiment is the same as the operating arm section 100 according to the first embodiment described above, and a description thereof will thus be omitted. Hereinafter, referring to FIG. 6, the medical arm assembly 5 according to the fifth embodiment will be described, focusing on differences from the third embodiment.

The positioning arm section 200 of the medical arm assembly 5 according to the fifth embodiment is configured as a 1-DOF Scott mechanism. For example, the joint B7 of the Scott mechanism performs a brake function and the joint B4 or the joint B7 performs a brake function so as to fix the position of the remote point RCM. In the fifth embodiment, the brake function is capable of being performed by restricting the operation of at least one of the joints B4, B5, B6, and B7 of the positioning arm section 200. For example, the brake function is capable of being performed by restricting the rotation of the rotating link 240 at the joint B4. In the medical arm assembly 5, a support joint J0, a joint A1, and a joint A2 are independent joints, and a joint A3 and a remote joint J1 are dependent joints.

In addition, any one of the joints B4, B5, B6, and B7 is an independent joint and the remaining three are dependent joints. For example, the joint B4 may be an independent joint, and the joint B5, the joint B6, and the joint B7 may be dependent joints that are passively operated by the operation of the joint B4. In another example, the joint B7 may be an independent joint, and the joint B4, the joint B5, and the joint B6 may be dependent joints that are passively operated by the operation of the joint B7. The joint B4, the joint B5, the joint B6, and the joint B7 may be set such that, according to the operation of any one of the joint B4, the joint B5, the joint B6, and the joint B7, the operation of the remaining three joints are performed via a gear, a belt, a pulley, or the like. Thereby, the remote point RCM becomes movable only along one reference straight line X. The positioning arm section 200 is capable of being operated by only one positioning motor of the medical arm assembly 5.

The arm supporting section 10 of the medical arm assembly 5 includes a rearward end portion 11 extending along the reference straight line X and an extension 13 extending in a direction crossing the reference straight line X at the rearward end portion 11. For example, the extension 13 may extend upwards from the rearward end portion 11. The extension 13 and the rearward end portion 11 are fixedly connected to each other. The extension 13 and the rearward end portion 11 may be integrally formed with each other.

The positioning arm section 200 of the medical arm assembly 5 includes a guide link 250 connected to the remote joint J1. The guide link 250 may be connected to the hinge part J1a of the remote joint J1 at one end thereof.

The guide link 250 of the medical arm assembly 5 is connected to the rotating link 240 so as to be rotatable about a guide rotation axis. The guide link 250 is connected to the rotating link 240 by the joint B5. The joint B5 includes a hinge having the guide rotation axis. The guide rotation axis may extend in a direction perpendicular to the reference axis X. The guide rotation axis may be parallel to the remote rotation axis.

The guide link 250 includes a forward end portion 252 and a rearward end portion 251 with respect to the joint B5. The forward end portion 252 is connected to the remote joint J1. The rearward end portion 251 is connected to the joint B6.

The positioning arm section 200 of the medical arm assembly 5 includes the rotating link 240 connected to the guide link 250 so as to be rotatable about the guide rotation axis. The rotating link 240 is connected to the arm supporting section 10 so as to be rotatable about a rotation axis parallel to the guide rotation axis. The rotating link 240 is connected to the arm supporting section 10 by the joint B4. The joint B4 includes a hinge having a rotation axis parallel to the guide rotation axis.

The positioning arm section 200 of the medical arm assembly 5 further includes a sliding link 260 connected to the arm supporting section 10 so as to be movable in a direction perpendicular to the guide rotation axis. The sliding link 260 is connected to the arm supporting section 10 by the joint B7. The joint B7 includes a guide configured to guide the movement of the sliding link 260 in the direction perpendicular to the guide rotation axis.

The sliding link 260 is connected to the guide link 250 so as to be rotatable about a rotation axis parallel to the guide rotation axis. The sliding link 260 is connected to the guide link 250 by the joint B6. The joint B6 includes a hinge having a rotation axis parallel to the guide rotation axis.

With reference to the connection point between the guide link 250 and the rotating link 240 (the point where the joint B5 is located), the connection point between the guide link 250 and the sliding link 260 (the point where the joint B6 is located) is located on an opposite side of the remote joint J1. The sliding link 260 may be located behind the joint B5. The direction perpendicular to the guide rotation axis may be the upward-and-downward direction.

Figure 7:
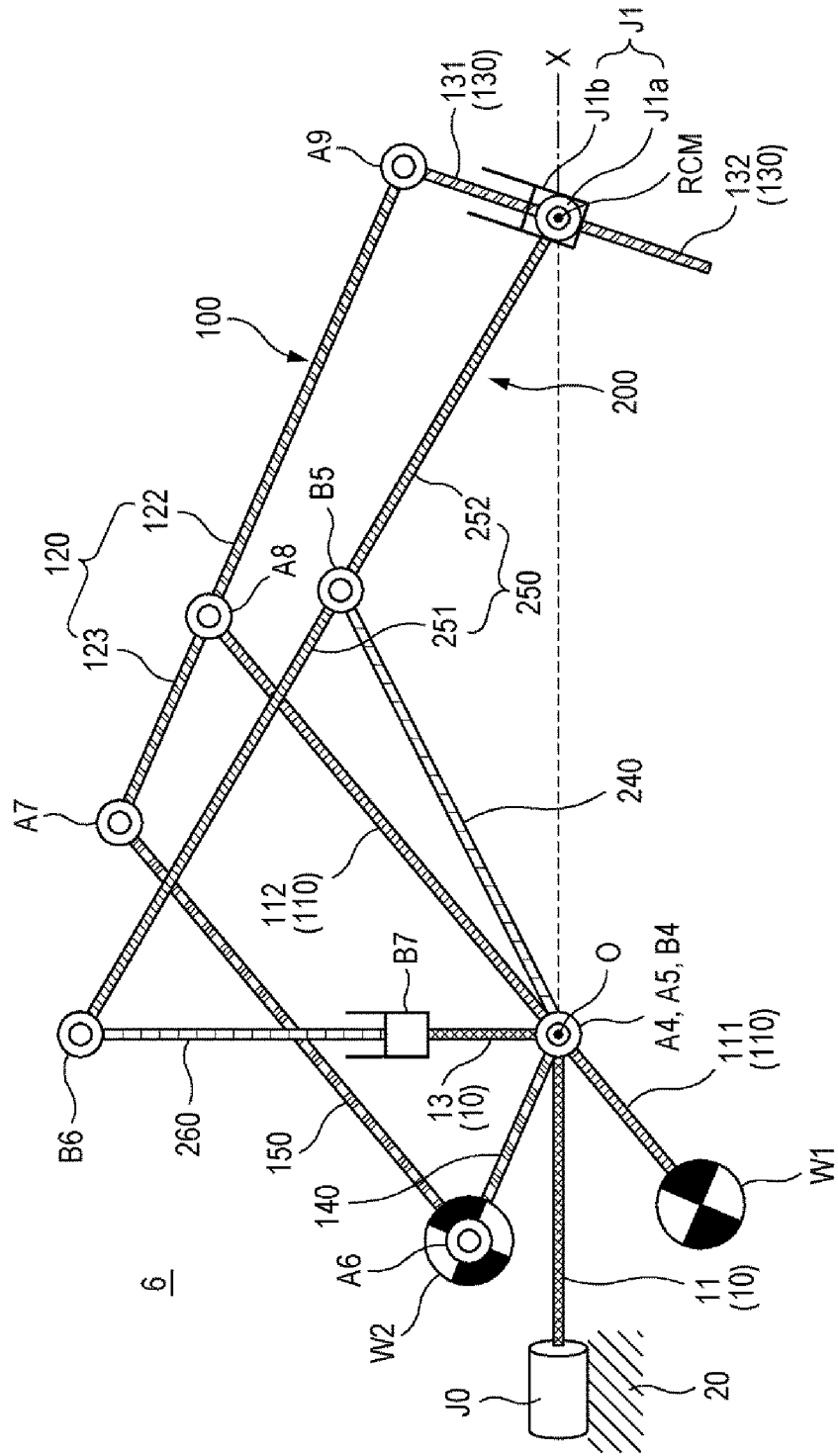
FIG. 7 is a conceptual elevation illustrating a medical arm assembly 6 according to a sixth embodiment of the present disclosure.

FIG. 7 is a conceptual elevation illustrating a medical arm assembly 6 according to a sixth embodiment of the present disclosure. The operating arm section 100 of the medical arm assembly 6 according to the sixth embodiment is the same as the operating arm section 100 according to the second embodiment described above, and a description thereof will thus be omitted. The positioning arm section 200 of the medical arm assembly 6 according to the sixth embodiment is the same as the positioning arm section 200 according to the fifth embodiment described above, and a description thereof will thus be omitted.

Figure 8:
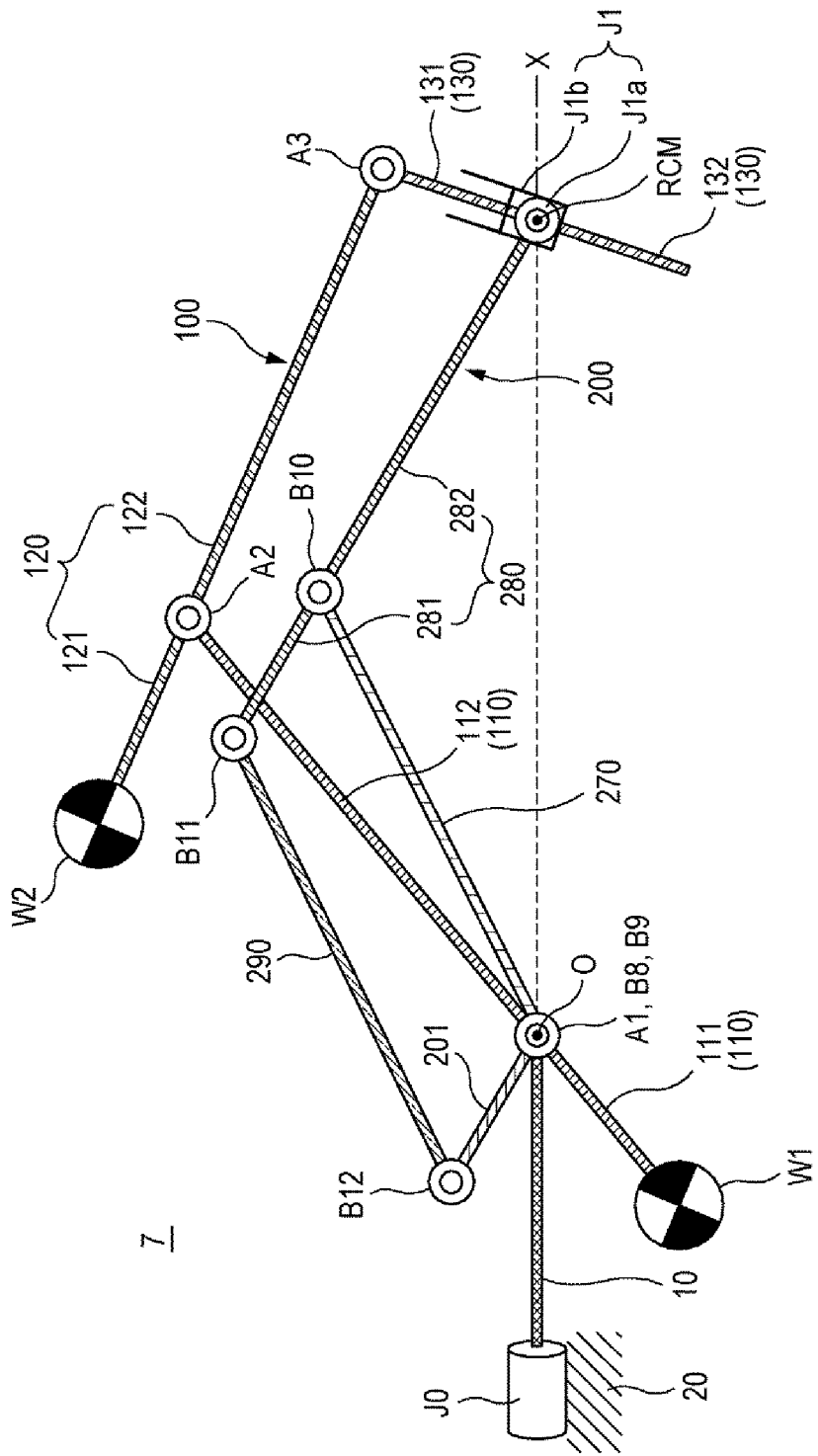
FIG. 8 is a conceptual elevation illustrating a medical arm assembly 7 according to a seventh embodiment of the present disclosure.

FIG. 8 is a conceptual elevation illustrating a medical arm assembly 7 according to a seventh embodiment of the present disclosure. The operating arm section 100 of the medical arm assembly 7 according to the seventh embodiment is the same as the operating arm section 100 according to the first embodiment described above, and a description thereof will thus be omitted. Hereinafter, referring to FIG. 8, the medical arm assembly 7 according to the seventh embodiment will be described, focusing on differences from the third embodiment.

The positioning arm section 200 of the medical arm assembly 7 according to the seventh embodiment includes four bars with 1 DOF having a braking function. In the seventh embodiment, the brake function is capable of being performed by restricting the operation of at least one of the joints B8 and B9 of the positioning arm section 200. For example, the brake function is capable of being performed by restricting the rotation of the rotating link 270 at the joint B8. In the medical arm assembly 7, a support joint J0, a joint A1, and a joint A2 are independent joints, and a joint A3 and a remote joint J1 are dependent joints.

In addition, any one of the joints B8, B9, B10, B11, and B12 is an independent joint and the remaining four are dependent joints. For example, the joint B8 may be an independent joint, and the joint B9, the joint B10, the joint B11, and the joint B12 may be dependent joints that are passively operated by the operation of the joint B8. In another example, the joint B9 may be an independent joint, and the joint B8, the joint B10, the joint B11, and the joint B12 may be dependent joints that are passively operated by the operation of the joint B9.

In an example, the rotation of the joint B9 may be set to be performed in accordance with the rotation of the joint B8 through a belt and a pulley. In another example, the rotation of the joint B9 may be set to be performed in accordance with the rotation of the joint B8 through a plurality of gears such as a bevel gear and a spur gear.

When the joint B8 rotates the rotating link 270 in a specific rotation direction and at a specific rotating speed with respect to the arm supporting section 10, at the joint B9, the first operating link 201 may be set to rotate in an opposite direction of the specific rotation direction but at the same rotating speed as the specific rotating speed with respect to the arm supporting section 10. Thereby, the remote point RCM becomes movable only along one reference straight line X. The positioning arm section 200 is capable of being operated using only one positioning motor of the medical arm assembly 5.

The joint A1, the joint B8, and the joint B9 may be disposed at the distal end of the arm supporting section 10 of the medical arm assembly 7. The support joint J0 may be connected to the rearward end of the arm supporting section 10 of the medical arm assembly 7, and the joint A1, the joint B8, and the joint B9 may be connected to the forward end of the arm supporting section 10.

The positioning arm section 200 of the medical arm assembly 7 includes a guide link 280 connected to the remote joint J1. The guide link 280 may be connected to the hinge part J1a of the remote joint J1 at one end thereof.

The guide link 280 of the medical arm assembly 7 is connected to the rotating link 270 so as to be rotatable about a guide rotation axis. The guide link 280 is connected to the rotating link 270 by the joint B10. The joint B10 includes a hinge having the guide rotation axis. The guide rotation axis may extend in a direction perpendicular to the reference axis X. The guide rotation axis may be parallel to the remote rotation axis.

The guide link 280 includes a forward end portion 282 and a rearward end portion 281 with respect to the joint B10. The forward end portion 282 is connected to the remote joint J1. The rearward end portion 281 is connected to the joint B11.

The positioning arm section 200 of the medical arm assembly 7 includes the rotating link 270 connected to the guide link 280 so as to be rotatable about the guide rotation axis. The rotating link 270 is connected to the arm supporting section 10 so as to be rotatable about a rotation axis parallel to the guide rotation axis. The rotating link 270 is connected to the arm supporting section 10 by the joint B8. The joint B8 includes a hinge having a rotation axis parallel to the guide rotation axis.

The positioning arm section 200 of the medical arm assembly 7 further includes a first operating link 201 connected to the arm supporting section 10 so as to be rotatable about a rotation axis parallel to the guide rotation axis. The first operating link 201 is connected to the arm supporting section 10 by the joint B9. The joint B9 includes a hinge having a rotation axis parallel to the guide rotation axis.

The positioning arm section 200 of the medical arm assembly 7 includes a second operating link 290 connected to the first operating link 201 so as to be rotatable about a rotation axis parallel to the guide rotation axis. The second operating link 290 is connected to the first operating link 201 by the joint B12. The joint B12 includes a hinge having a rotation axis parallel to the guide rotation axis.

The second operating link 290 is connected to a guide link 280 so as to be rotatable about a rotation axis parallel to the guide rotation axis. The second operating link 290 is connected to the guide link 280 by the joint B11. The joint B11 includes a hinge having a rotation axis parallel to the guide rotation axis.

With reference to the connection point between the guide link 280 and the rotating link 270 (the point where the joint B10 is located), the connection point between the guide link 280 and the second operating link 290 (the point where the joint B11 is located) is located on an opposite side of the remote joint J1. The joint B12 is located behind the joint A11 and the joint B9.

Figure 9:
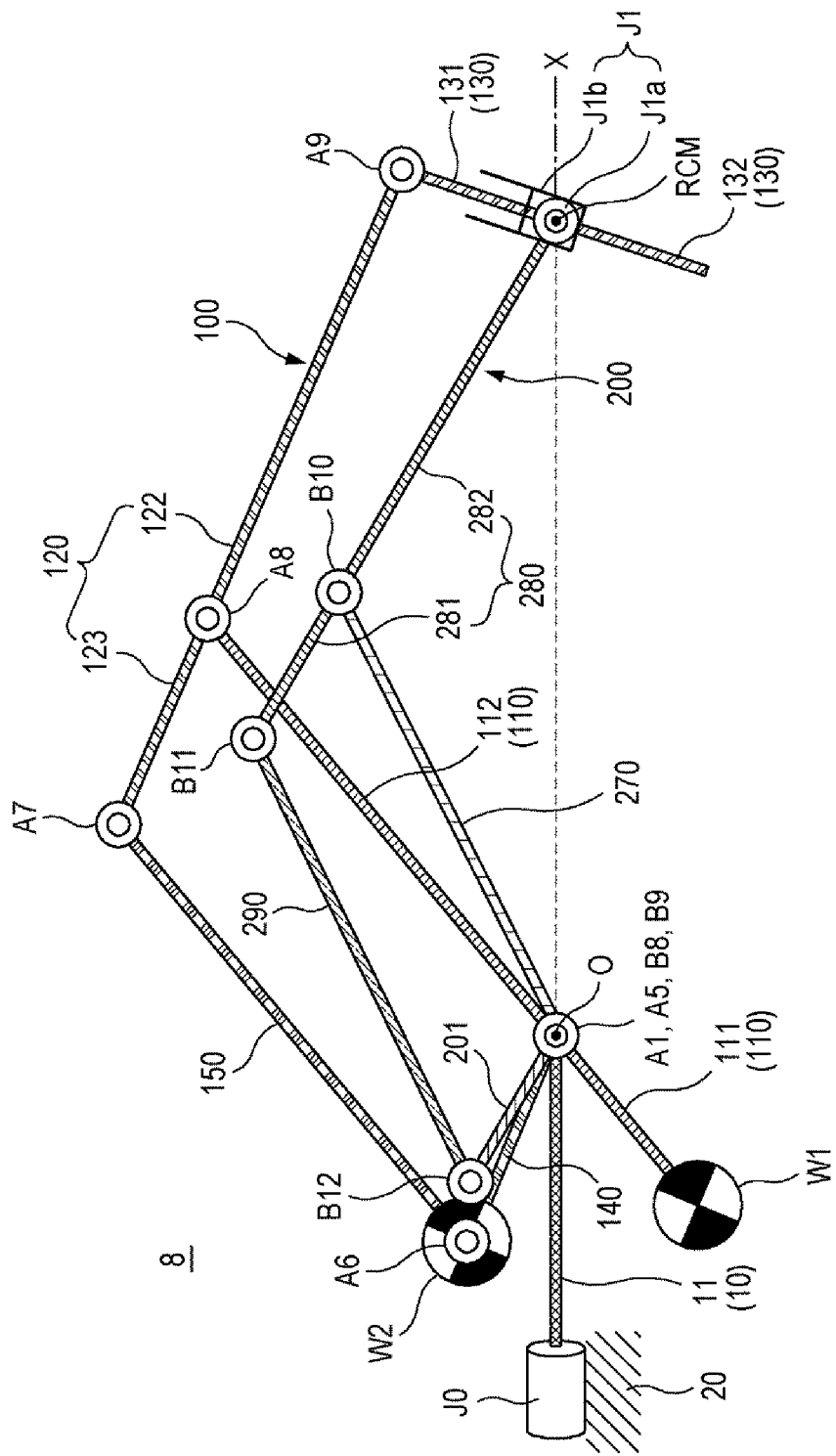
FIG. 9 is a conceptual elevation illustrating a medical arm assembly 8 according to an eighth embodiment of the present disclosure.

FIG. 9 is a conceptual elevation illustrating a medical arm assembly 8 according to an eighth embodiment of the present disclosure. The operating arm section 100 of the medical arm assembly 8 according to the eighth embodiment is the same as the operating arm section 100 according to the second embodiment described above, and a description thereof will thus be omitted. The positioning arm section 200 of the medical arm assembly 8 according to the eighth embodiment is the same as the positioning arm section 200 according to the seventh embodiment described above, and a description thereof will thus be omitted.

Figure 10A:
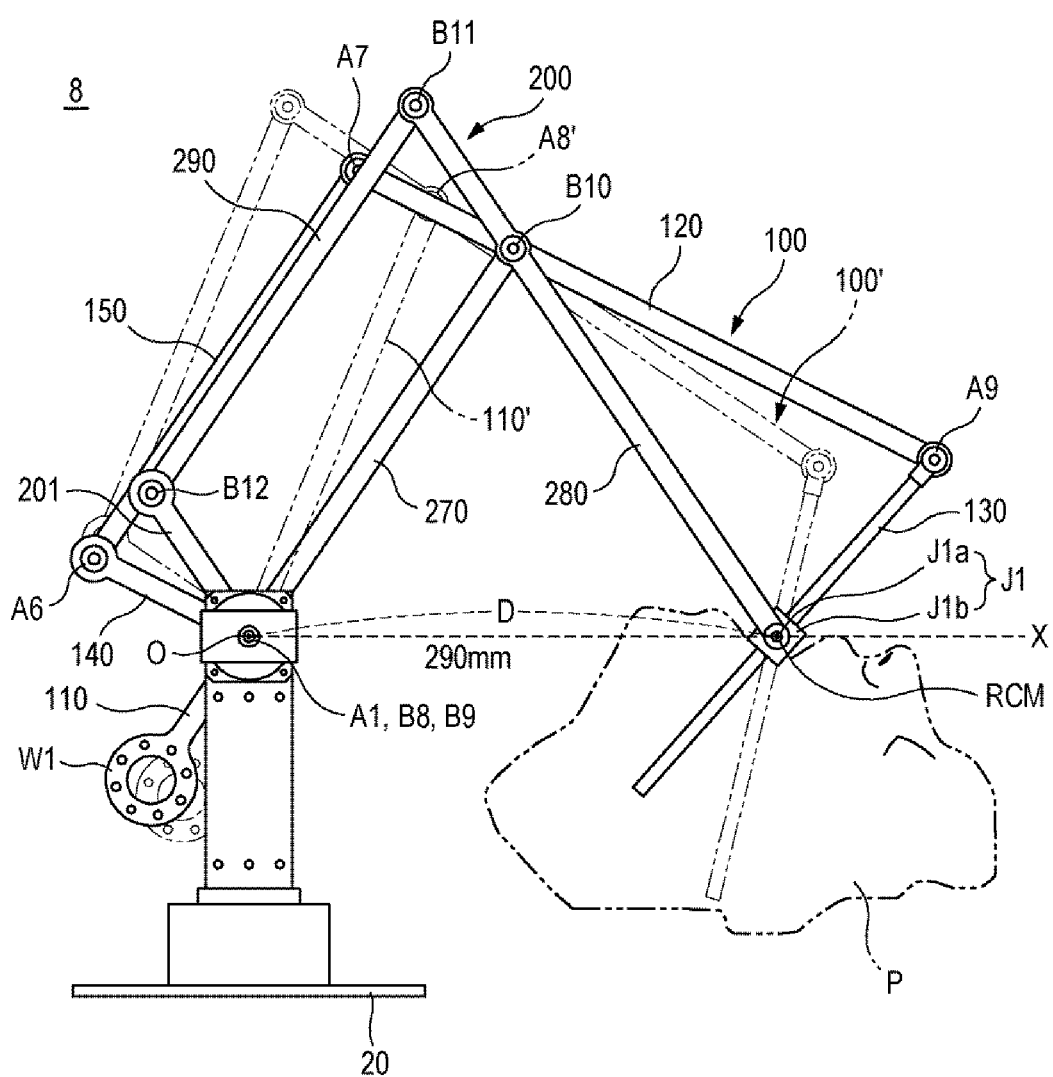
FIGS. 10A and 10B are elevations each illustrating an operating mechanism of the medical arm assembly 8 according to the eighth embodiment of the present disclosure.
Figure 10B:
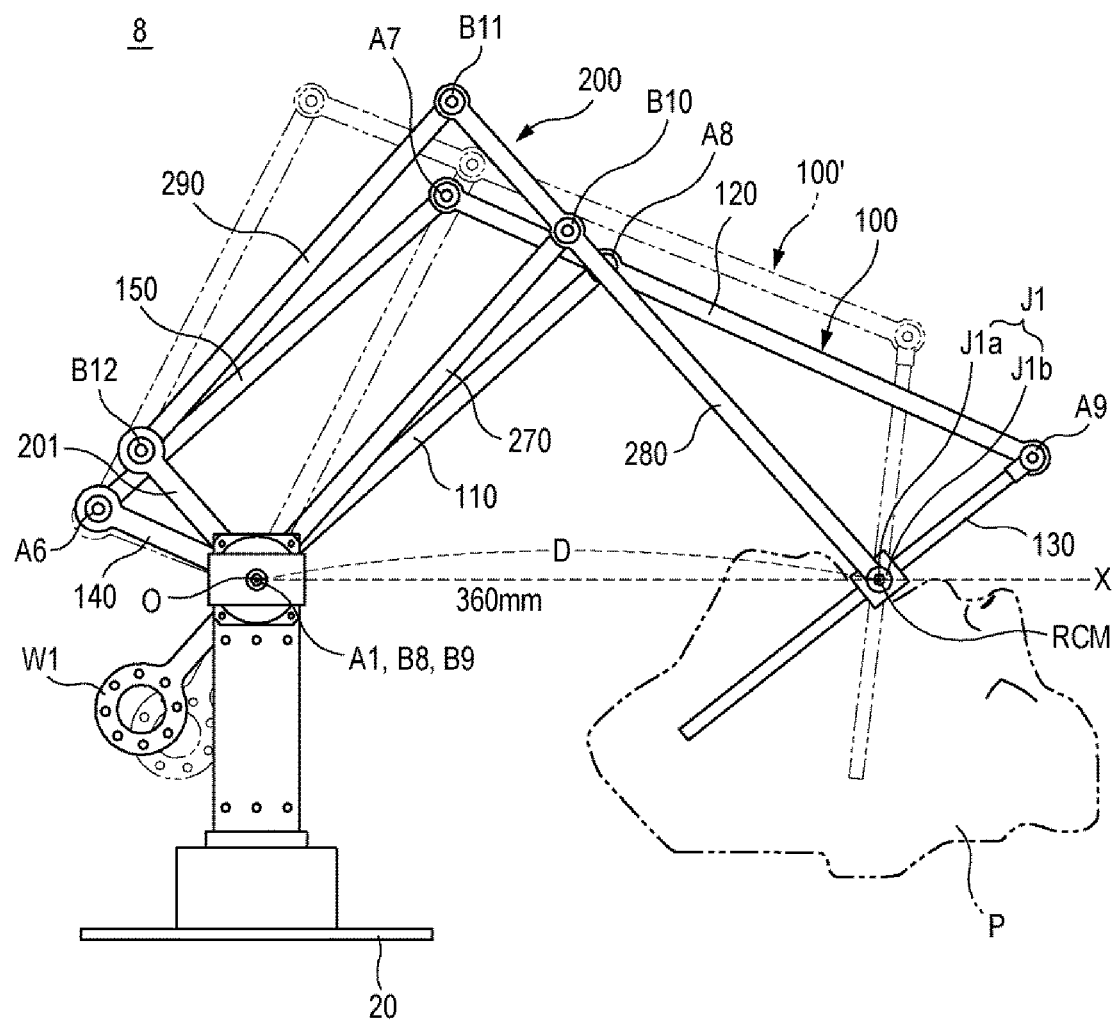

FIGS. 10A and 10B are elevations each illustrating an operating mechanism of the medical arm assembly 8 according to the eighth embodiment of the present disclosure. In FIG. 10A, the distance D between the reference point O and the remote point RCM is about 290 mm, and in FIG. 10B, the distance D between the reference point O and the remote point RCM is about 360 mm. The state of FIG. 10B is obtained when the positioning arm section 200 is operated so as to change from the state of FIG. 10A so that the relative position of the remote point RCM with respect to the reference point O is changed on the reference straight line X. In each of the states of FIGS. 10A and 10B, the positioning arm section 200 is capable of fixing the relative position of the remote point RCM by the brake function. In the state in which the relative position of the remote point RCM is fixed, the ending link 130, at which the tool is fixed, is capable of performing the above-mentioned 3-DOF motion by causing the operating arm section 100 and the arm supporting section to operate. An operation arm section 100' indicated by adding a comma (') to the reference numeral in FIGS. 10A and 10B shows, by a dotted line, an exemplary figure according to an operation of the operation arm section 100 in the fixed state of the remote point RCM.

Although the technical idea of the present disclosure has been described above with reference to some embodiments and examples illustrated in the accompanying drawings, it should be understood that various substitutions, changes, and alterations can be made without departing from the technical idea and scope of the present disclosure. It should also be understood that such substitutions, modifications and variations are intended to fall within the scope of the present disclosure, which is defined in the accompanying claims.

What is claimed is:

1. A medical arm assembly comprising:
   a remote joint in which a remote point spaced apart from a reference point is located;
   a positioning arm section configured to support the remote joint, move the remote joint such that a relative position of the remote point with respect to the reference point is changed only in a direction of a virtual reference straight line passing through the reference point and the remote point, and fix the relative position of the remote point with respect to the reference point;
   an operating arm section connected to the remote joint, the operating arm section being configured to fix a medical tool thereto and rotate the tool about a remote rotation axis that is perpendicular to the reference straight line and passes through the remote point, the operating arm section being configured to move the tool in a direction that is perpendicular to the remote rotation axis and passes through the remote point; and
   an arm supporting section, to which the positioning arm section and the operating arm section are connected to be supported, the reference point being located in the arm supporting section.

2. The medical arm assembly of claim 1, wherein the arm supporting section is configured to be rotatable about the reference straight line.

3. The medical arm assembly of claim 2, further comprising:
   an arm supporting section motor configured to provide a driving force for rotating the arm supporting section about the reference straight line.

4. The medical arm assembly of claim 1, wherein the positioning arm section includes a positioning motor configured to provide a driving force so as to change the relative position of the remote point.

5. The medical arm assembly of claim 1, wherein the operating arm section includes an ending link slidably supported on the remote joint, and the positioning arm section includes a guide link connected to the remote joint.

6. The medical arm assembly of claim 5, wherein the ending link is configured to be rotatable about the remote rotation axis and to be movable in a direction that is perpendicular to the remote rotation axis and passes through the remote point.

7. The medical arm assembly of claim 5, wherein the remote joint includes:

a sliding part configured to slidably support the ending link, and a hinge part configured to rotatably connect the guide link to the sliding part.

8. The medical arm assembly of claim 1, wherein the operating arm section includes:

an ending link slidably supported on the remote joint;

a middle link connected to the ending link so as to be rotatable about a rotation axis parallel to the remote rotation axis; and a starting link connected to the middle link so as to be rotatable about the rotation axis parallel to the remote rotation axis and connected to the arm supporting section so as to be rotatable about the rotation axis parallel to the remote rotation axis.

9. The medical arm assembly of claim 8, wherein the operating arm section further includes:

a first counterweight configured to provide a gravity load such that a connection point between the starting link and the middle link is lifted upwards; and a second counterweight configured to provide a gravity load such that a connection point between the middle link and the ending link is lifted upwards.

10. The medical arm assembly of claim 8, wherein the operating arm section further includes:

a first operating motor configured to provide a driving force for rotating the starting link with respect to the arm supporting section; and a second operating motor configured to provide a driving force for rotating the middle link with respect to the starting link.

11. The medical arm assembly of claim 8, wherein the operating arm section further includes:

a first link connected to the arm supporting section so as to be rotatable about the rotation axis parallel to the remote rotation axis; and a second link connected to the first link so as to be rotatable about the rotation axis parallel to the remote rotation axis, and connected to the middle link so as to be rotatable about the rotation axis parallel to the remote rotation axis, and wherein, with reference to a connection point between the middle link and the starting link, a connection point between the middle link and the second link is located on an opposite side of a connection point between the middle link and the ending link.

12. The medical arm assembly of claim 1, wherein the positioning arm section includes a guide link, connected to the remote joint and connected to the arm supporting section so as to be movable in the direction of the reference straight line.

13. The medical arm assembly of claim 1, wherein the positioning arm section includes:

a guide link connected to the remote joint; and a rotating link connected to the guide link so as to be rotatable about a guide rotation axis and connected to the arm supporting section so as to be rotatable about a rotation axis parallel to the guide rotation axis.

14. The medical arm assembly of claim 13, wherein the positioning arm section further includes a sliding link connected to the arm supporting section so as to be movable in a direction perpendicular to the guide rotation axis and connected to the guide link so as to be rotatable about a rotation axis parallel to the guide rotation axis, wherein, with reference to a connection point between the guide link and the rotating link, a connection point between the guide link and the sliding link is located on an opposite side of the remote joint.

15. The medical arm assembly of claim 13, wherein the positioning arm section further includes:

a first operating link connected to the arm supporting section so as to be rotatable about a rotation axis parallel to the guide rotation axis; and a second operating link connected to the first operating link so as to be rotatable about a rotation axis parallel to the guide rotation axis, and connected to the guide link so as to be rotatable about a rotation axis parallel to the guide rotation axis, and wherein, with reference to a connection point between the guide link and the rotating link, a connection point between the guide link and the second operating link is located on an opposite side of the remote joint.

* * * * *